(12) United States Patent
Johnson (10) Patent No.: US 11,173,235 B2
(45) Date of Patent: Nov. 16, 2021

(54) NITRITE ELUTING DEVICES AND METHODS OF USE THEREOF

(71) Applicant: COOK REGENTEC LLC, Indianapolis, IN (US)

(72) Inventor: Chad E. Johnson, West Lafayette, IN (US)

(73) Assignee: Cook Regentec LLC, Indianapolis, IN (US)

( * ) Notice: Subject to any disclaimer, the term of this patent is extended or adjusted under 35 U.S.C. 154(b) by 237 days.

(21) Appl. No.: 15/641,789

(22) Filed: Jul. 5, 2017

(65) Prior Publication Data

US 2018/0015209 A1 Jan. 18, 2018

Related U.S. Application Data

(60) Provisional application No. 62/362,966, filed on Jul. 15, 2016.

(51) Int. Cl.
| | |
|---|---|
| *A61F 2/82* | (2013.01) |
| *A61L 31/08* | (2006.01) |
| *A61L 29/08* | (2006.01) |
| *A61F 2/89* | (2013.01) |
| *A61K 31/337* | (2006.01) |
| *A61K 33/00* | (2006.01) |
| *A61L 29/10* | (2006.01) |
| *A61L 29/16* | (2006.01) |
| *A61L 31/16* | (2006.01) |
| *A61M 25/10* | (2013.01) |

(Continued)

(52) U.S. Cl.
CPC .............. *A61L 31/088* (2013.01); *A61F 2/89* (2013.01); *A61K 31/337* (2013.01); *A61K 33/00* (2013.01); *A61L 29/08* (2013.01); *A61L 29/106* (2013.01); *A61L 29/16* (2013.01); *A61L 31/08* (2013.01); *A61L 31/16* (2013.01); *A61M 25/10* (2013.01); *C01B 21/22* (2013.01); *C01B 21/50* (2013.01); *A61F 2002/047* (2013.01); *A61F 2310/0097* (2013.01); *A61L 2300/114* (2013.01); *A61L 2300/208* (2013.01); *A61L 2300/416* (2013.01)

(58) Field of Classification Search
CPC .................................. A61F 2/82; A61L 31/08
See application file for complete search history.

(56) References Cited

U.S. PATENT DOCUMENTS 5,639,577 A 6/1997 Takeuchi et al.
5,820,918 A 10/1998 Ronan et al.
(Continued)

FOREIGN PATENT DOCUMENTS

EP 3 085 395 A1 10/2016
WO WO 2009/131931 A 10/2009

OTHER PUBLICATIONS

Extended European Search Report in corresponding European Application No. 17181745.5, dated Mar. 12, 2018, 12 pages.

(Continued)

*Primary Examiner* — Matthew W Schall
(74) *Attorney, Agent, or Firm* — Crowell & Moring LLP (57) ABSTRACT

The present disclosure generally relates to implantable devices including a releasable nitrite ion and to methods of preparing and using such compositions and devices. In one embodiment, the device is a stent, for example, a vascular stent. In another embodiment, the nitrite ion is ionically bound to an inorganic ion.

16 Claims, 5 Drawing Sheets

(51) Int. Cl.
*C01B 21/22* (2006.01)
*C01B 21/50* (2006.01)
*A61F 2/04* (2013.01)

(56) References Cited

U.S. PATENT DOCUMENTS

| | | | |
|---|---|---|---|
| 5,994,444 A | 11/1999 | Trescony et al. | |
| 6,057,367 A | 5/2000 | Stamler et al. | |
| 6,087,479 A | 7/2000 | Stamler et al. | |
| 6,103,275 A | 8/2000 | Seitz et al. | |
| 6,471,978 B1 | 10/2002 | Stamler et al. | |
| 6,599,878 B2 | 7/2003 | Rooney | |
| 7,048,951 B1 | 5/2006 | Seitz et al. | |
| 7,138,430 B2 | 11/2006 | Garvey | |
| 7,399,296 B2 | 7/2008 | Poole et al. | |
| 7,794,490 B2 * | 9/2010 | King | A61F 2/06 623/1.13 |
| 8,329,543 B2 | 12/2012 | Kang et al. | |
| 8,591,932 B2 | 11/2013 | Cleek et al. | |
| 8,697,771 B2 | 4/2014 | Meyerhoff et al. | |
| 8,771,756 B2 | 7/2014 | Reynolds et al. | |
| 2003/0022267 A1 | 1/2003 | Stamler et al. | |
| 2003/0072783 A1 | 4/2003 | Stamler et al. | |
| 2005/0265958 A1 | 12/2005 | West et al. | |
| 2006/0182815 A1 * | 8/2006 | Gladwin | A61K 31/519 424/718 |
| 2007/0239107 A1 | 10/2007 | Lundberg et al. | |
| 2007/0248676 A1 | 10/2007 | Stamler | |
| 2008/0286333 A1 * | 11/2008 | Kangas | A61L 27/54 424/425 |
| 2009/0255536 A1 | 10/2009 | Av-Gay et al. | |
| 2010/0049296 A1 | 2/2010 | Sarasam et al. | |
| 2012/0193125 A1 | 8/2012 | Pavlovic et al. | |
| 2014/0308260 A1 | 10/2014 | Oronsky et al. | |

OTHER PUBLICATIONS

Partial European Search Report in corresponding European Application No. 17181745.5, dated Dec. 4, 2017, 14 pages.

* cited by examiner

NITRITE ELUTING DEVICES AND METHODS OF USE THEREOF

RELATED APPLICATIONS

This non-provisional patent application claims priority to U.S. Provisional Patent Application No. 62/362,966, filed Jul. 15, 2016, the contents of which are incorporated by reference in their entirety.

TECHNICAL FIELD

The present disclosure generally relates to implantable devices including a releasable nitrite ion and to methods of preparing and using such devices.

BACKGROUND

Local delivery of a therapeutic agent can be useful in the treatment of many medical conditions. For example, local delivery of a therapeutic agent within a body vessel or to a selected portion of internal body tissue can eliminate or reduce the need for systemic delivery of the agent thus minimizing any potential adverse effect of the agent on areas of the body not needing treatment.

Minimally invasive implantable medical devices, such as balloons, catheters and stents, can provide a platform for delivering such therapeutic agents to internal body tissue. For example, balloon catheters or stents may be used to deliver a therapeutic agent directly to the target site within a body vessel such as an artery or vein.

One example of a condition that can be beneficially treated by local administration of a therapeutic agent with a balloon catheter or stent is the delivery of a therapeutic agent in combination with percutaneous transluminal coronary angioplasty (PTCA), a technique used to dilate stenotic portions of blood vessels. Although PTCA and related procedures aid in alleviating intraluminal constrictions, such constrictions or blockages may reoccur over time in many cases. The cause of these recurring obstructions, termed restenosis, may be due to the body responding to the surgical procedure. Restenosis of the vessel may develop over several months after the procedure, and may require another angioplasty procedure or a surgical bypass operation to correct.

Proliferation and migration of smooth muscle cells (SMC) from the media layer of the lumen to the intimal layer cause an excessive production of extracellular matrices (ECM), which is believed to be one of the leading contributors to the development of restenosis. The extensive thickening of tissue narrows the lumen of the blood vessel, constricting or blocking the blood flow through the vessel.

Drugs that inhibit restenosis may be locally delivered during PTCA from a catheter or by placement of a stent configured to continue to release the drug after the PTCA procedure. The delivery of the drug from coatings in these and other minimally invasive procedures can be complicated by the need both to have a coating that is durable during delivery, but which effectively delivers the drug when implanted in the region where local treatment is desired.

Nitric oxide-based treatment for the treatment of cardiovascular pathologies has shown promise in the treatment of restenosis. For example, the use of drug nitric oxide eluting stents allowing for the local delivery of nitric oxide to a vessel wall had been proposed. However, the difficulty in controlled, local release of nitric oxide has limited their clinical use.

SUMMARY

One aspect of the present invention relates to a medical device including a base structure and at least one surface having a coating including a compound including a nitrite ion ionically bonded thereto. In a preferred embodiment, the medical device, including the coating, is free of a nitric oxide generator.

The compound including the nitrite ion may be an organic compound or an inorganic compound. The organic compound may be any of a variety of secondary amine nitrites, for example dicyclohexylamine nitrite, or quarternary ammonium nitrites, for example tetrabutylammonium nitrite. The inorganic compound may be, for example sodium nitrite, lithium nitrite, potassium nitrite, calcium nitrite, magnesium nitrite, ammonium nitrite, nitrous acid, nickel nitrite, or silver nitrite.

In one embodiment, the coating consists essentially of the compound. In another embodiment, the coating further includes a polymeric or non-polymeric carrier matrix. In yet another embodiment, the coating is free of a polymer or non-polymer carrier matrix.

The medical device may be, for example, a stent, a vascular stent, a ureteral stent, a catheter, a balloon, a balloon catheter, a stent graft, a wire guide or a cannula.

In some embodiments the device also includes a drug, for example, an immunosuppressive agent, an antiproliferative agent, a microtubule stabilizing agent, a restenosis-inhibiting agent, a taxane compound, such as paclitaxel, or an inhibitor of the mammalian target of rapamycin.

Another aspect of the invention provides a method for delivering a nitrite ion locally to tissue of a patient. The method includes contacting a vessel wall of the patient with the medical device as disclosed herein and maintaining the device in contact with the vessel wall for a time sufficient to deliver the nitrite ion to the tissue of the patient.

Yet another aspect of the invention provides a method for treating a patient suffering from a vascular disease or condition. The method includes contacting a vessel wall of the patient with the medical device as disclosed herein and maintaining device within the body of the patient for a time sufficient to deliver a therapeutically effective amount of the nitrite ion to tissue of the patient. In one embodiment, the vascular disease or condition is restenosis. In another embodiment, the device is free of a nitric oxide generator.

DETAILED DESCRIPTION OF THE PREFERRED EMBODIMENTS

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In the discussions that follow, a number of potential features or selections of the drug, excipient, implantable medical device structure, or other aspects, are disclosed. It is to be understood that each such disclosed feature or features can be combined with the generalized features discussed herein, to form a disclosed embodiment of the present invention.

Definitions

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a nitrite ion means an amount of the nitrite ion which imparts a therapeutic effect to the human or veterinary patient when delivered to the patient as described herein.

The term "bioabsorbable" is used herein to refer to materials that dissipate upon implantation within a body, independent of which mechanisms by which dissipation can occur, such as dissolution, degradation, absorption and excretion.

As used herein, the term "body vessel" means a body lumen, including but not limited to blood vessels, esophageal, intestinal, biliary, urethral and ureteral passages.

Medical Devices including a Releasable Nitrite Ion

One aspect of the present invention provides a medical device including a releasable nitrite ion (Nitrite, $NO_2^-$). In one embodiment, the nitrite ion is released from the device when at least a portion of the device is implanted into the body of a human or veterinary patient. In certain embodiments, the nitrite may be released over an extended period of time after implantation.

In one preferred embodiment, the device is free of any compound that acts on the nitrite ion, or any other component of the device, to produce nitric oxide or to release nitric oxide from the device. In such embodiments, the nitrite ion is released from the device after implantation and, depending on the local environmental conditions, is converted to nitric oxide through the normal intrinsic biochemical pathways of the body. However, the present invention also includes embodiments where a nitric oxide generator is present in the medical device. In prepared embodiments, direct nitric oxide synthesis by the device is limited as the main mode of action is through nitrite ion, and not nitric oxide, delivery. In those embodiments including a nitric oxide generator, the amount of nitric oxide generator is such that less than 10 or 5 or 1 percentage of the maximum nitric oxide generated by the device is generated by direct release of nitric oxide (as opposed to conversion of nitrite ion release from the device.) As used herein, the term nitric oxide generator includes any compound that chemically reacts with the nitrite ion or any other component of the medical device to produce nitric oxide.

Nitrite is a common molecule that can be found in many food items as well as exists in low quantities in the blood. Under the right conditions, nitrite is converted to nitric oxide. This can happen through enzyme mediated events or through non-catalyzed reactions. Specifically, nitrite has been shown to be converted to nitric oxide in acidic conditions, through reducing agents, and through enzymatic reactions specifically in the presence of high concentrations of carbon dioxide. As such, nitrite appears to be a natural reservoir for nitric oxide that is able to respond quickly to changing metabolic needs.

The balance of nitric oxide release to metabolic load is well controlled under normal conditions. This allows for quick response to muscle usage (e.g., exercise) that would subsequently result in vascular relaxation and additional regional blood flow. However, normal levels of circulating or resident nitrite can be quickly exhausted in situations such as injury, thereby altering the signaling state from maintenance (senescent) to proliferative (e.g. healing). Under most conditions, this response is the desired and useful response, however, in certain situations, this can become deleterious. One such example is vascular stenting, where the mechanical injury can lead to intimal hyperplasia and subsequent restenosis.

Nitrite release into the local environment for the body helps to reduce the proliferative response. The elevated local nitrite concentration can diffuse readily to the injured areas of the vessel. The mismatch of the high metabolism and lack of blood flow to the injured area of the vessel naturally creates a high carbon dioxide, low pH environment that results in the nitrite being converted to nitric oxide. The increased nitric oxide concentration subsequently signals the surrounding cells to differentiate and relax rather than proliferate. Additionally, the nitrite-induced nitric oxide signal potentiates the angiogenic response, ideally to gradually increase the regional blood flow rather than the overshoot of capillary vascularity traditionally witnessed with stenting procedures.

The delivery of the nitrite ion from an implantable device offers multiple advantages over the direct delivery of nitric oxide from the device. The nitrite ion is much more stable than nitric oxide, allowing it to penetrate further into tissues. This provides for therapeutic activity not just at the surface of the stent, balloon or other device, but potentially throughout the vascular wall (e.g., even in the adventitia).

Furthermore, the nitrite ion will only be converted to nitric oxide if the biochemical conditions are right (e.g. high carbon dioxide, low pH). Thus, the presence and dose of nitric oxide depends, at least in part, on the local environment, such as areas of injury (carbon dioxide buildup, lightly acidic) or high cell proliferation (high metabolic activity) where the activity of nitric oxide would be most beneficial. Nitric oxide is only created from the nitrite ion where it is required.

The nitrite ion is also less toxic than nitric oxide, potentially allowing for a higher dose without the safety concerns with nitric oxide, especially if there is a rapid bolus release from an implanted device. In addition, many nitrite containing compounds are very stable, allowing for the ease in the manufacture, sterilization, packaging and delivery of nitrite ion containing devices compared to devices containing nitric oxide or nitric oxide donors.

The device may include a nitrite ion that is ionically bonded to either an organic or inorganic counter ion to form an organic or inorganic ionic compound. Organic compounds include any of a variety of secondary amine nitrites with the basic structure of R,R'—N—ONO, for example dicyclohexylamine nitrite, or quarternary ammonium nitrites with a basic structure of R,R',R'',R'''—N—ONO, for example tetrabutylammonium nitrite (where the R, R',R'', R'''— groups may be the same or different alkyl or aryl groups). Inorganic compounds include, for example, nitrous acid, ammonium nitrite or any of a variety of metal nitrites, for example, sodium nitrite, lithium nitrite, potassium nitrite, calcium nitrite, magnesium nitrite, nickel nitrite, or silver nitrite.

In some embodiments, the nitrite is tethered to the device either through a carrier (e.g., degradable polymer) or alternatively directly in the device material, either through association or direct binding by positively charging the device to bind the negatively charged nitrite. In some embodiments, the nitrite ion is released in sufficiently quantity to effect local response (micromolar to millimolar quantities) over an extended period of time (weeks to months). However, in other embodiments, the nitrite ion is rapidly released from the device (less than a minute to several minutes). For example, there the nitrite compound is carrier by a balloon portion of a balloon catheter, release of the compound occurs during the time the balloon is inflated.

The medical device may be any of a wide variety of devices having a structure sized and shaped for temporary or permanent implantation in a human or veterinary patient. Medical devices having structures implantable in a bodily passage will often be used. The bodily passage may for example be a passage of the alimentary system, the urogenital system, the biliary system, or the cardiovascular system. Medical devices including a device structure implantable in the cardiovascular system are preferred, including, for example, those implantable in a vessel or chamber of the cardiovascular system. The passage may be, for example, a tubular passage such as an artery or vein, or may be a larger chamber such as a ventricle or atrium of the heart. Implantable medical devices that include structures that span or bridge between cardiovascular or other bodily passages are also contemplated. The implantable medical device can be adapted to be entirely or only partially implanted in a cardiovascular passage or other bodily passage.

The releasable nitrite component may be incorporated into the structure of the medical device and/or be present in a coating on one or more surfaces of the device. By way of example, the medical device can be or include a catheter, a wire guide, a stent, a coil, a needle, a graft, a filter, a balloon, a cutting balloon, a scoring balloon, a weeping (perfusion) balloon, or any combination of these. Suitable filters include for example vena cava filters such as the Cook CELECT® and Cook Gunther TULIP® and Cook Gianturco-Roehm Bird's NEST® filters available from Cook Medical, Bloomington Ind., USA. Suitable stents include those without a covering, for example the Cook ZILVER® Cook ZILVER®-PTX stents available from Cook Medical. Suitable stents also include those with a sheath covering. Suitable coils include embolization coils. Suitable wire guides include for instance traditional wire guides as well as wire guides with an attached expandable structure for expansion within a blood vessel lumen, such as a coil, where the expandable structure can optionally carry the coating or coatings as disclosed herein. These or other implants, in certain preferred embodiments, have at least a portion that is configured to expand during deployment so as to contact walls of the passage in which they are implanted to anchor within the passage. In this regard, both self-expanding and force-expandable (e.g. balloon-expandable) stents or other implantable medical devices are contemplated as being within the scope of embodiments of the present invention.

The medical device can also include an additional therapeutic compound. For example, the device may include a drug such an immunosuppressive agent, an antiproliferative agent, a microtubule stabilizing agent, a restenosis-inhibiting agent, or an inhibitor of the mammalian target of rapamycin. In one embodiment, the device includes a taxane compound, for example, paclitaxel.

The implantable medical device can be made from any suitable material or combination of materials. Illustratively, the implantable medical device can include a metal such as stainless steel, tantalum, titanium, NITINOL (a nickel-titanium alloy), cobalt, chromium, nickel, molybdenum, manganese, gold, platinum, inconel, iridium, silver, tungsten, elgiloy, alloys of any of these, or another biocompatible metal; carbon or carbon fiber; a calcium-containing inorganic material such as a ceramic; a material composed of ceramic and metallic components (cermet); or a polymeric material.

The material of construction for the implantable medical device structure can be biodegradable or non-biodegradable. Nonbiodegradable polymers that can be used include, for example, cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these. Biodegradable polymers that can be used include, for example, polylactic acid (PLA), polyglycolic acid (PGA), poly(lactic-co-glycolic acid) (PLGA), polyanhydride, polycaprolactone, polyhydroxybutyrate valerate, or mixtures of these. Biodegradable metals may also be used, including for example a biodegradable magnesium alloy.

In those embodiments in which the nitrite ion is contained in a coating layer, any of a wide variety of coating patterns may be used to constitute a coating on the medical device. The coating layer can be directly adhered to a surface of an implantable base structure of the medical device and provide an outermost surface over the implantable device, and constitute the entirety of the coating on the implantable device. In other embodiments, an overall coating on the implantable structure of the medical device can include one or more different coatings positioned underneath the layer including the nitrite (e.g. as in a polymeric or other primer coating, or a different drug coating, adhered directly to the surface of the medical device), one or more different coatings positioned overtop the layer including the nitrite ion (e.g. as in a polymeric or other protective or diffusion barrier coating), or both. As well, there may be one or more different coatings adjacent the layer including the nitrite ion, and/or multiple layers including the nitrite ion may be carried by the implantable medical device at locations discrete from one another.

The layer including the nitrite ion may be present in an aperture(s) such as a well(s), groove(s) or hole(s) defined in the implantable medical device (e.g. in a stent) or may partially coat or completely coat the implantable medical device or a given surface (e.g. inner, outer or side surface) of the implantable medical device. These and other overall device coating arrangements can be utilized.

The layer including the nitrite ion can be carried by any suitable surface of the implantable medical device structure. The layer including the nitrite ion can be carried by, and in some embodiments only by, a surface or surfaces of the implantable medical device configured for contact with patient tissue when the device is implanted. For example, in some embodiments the layer including the nitrite ion is carried by a surface of a balloon of a balloon catheter, or by a surface of a stent, which is configured for contact with a wall of a vessel when the balloon is implanted (usually temporarily) or when the stent is implanted (usually permanently). In particular embodiments, in the case of a balloon of a balloon catheter which inflates to provide a substantially cylindrical outer surface as discussed above, the layer including the nitrite ion is carried by such substantially cylindrical outer surface, either partially or completely covering the substantially cylindrical surface. In the case of a stent having an outer surface as discussed above, the layer including the nitrite ion can be carried by the outer surface, either partially or completely covering the outer surface.

The layer including the nitrite and any other coating layers present can be incorporated as a part of the implantable medical device by any suitable method. This layer and any other coating layer can be formed on a surface of the implantable medical device. For example, the layer or other coating layer(s) can be formed by a method that includes dipping, spraying, showering, dripping, or otherwise applying a medium containing the coating ingredients, and optionally a substance such as a solvent can be removed from the medium to leave the coating adhered to the implantable medical device. Spray coating is one preferred form of applying the coating materials to the surface of the implantable medical device, and in particular embodiments ultrasonic spray coating will be utilized. During spray coating or other coating operations, the implantable medical device can be moved relative to a sprayer or other applicator of the coating ingredients. This can occur by moving the implantable medical device (including for example rotating the device or at least the portion to be coated), moving the sprayer or other applicator, or both. Multiple application passes or steps will typically be utilized to increase the thickness of the layer including the releasable component or other coating layer(s) and control the levels of the nitrite, excipient, carrier, or other ingredients applied to the implantable medical device. In spray or other application processes, areas of the implantable medical device adjacent to areas desired for coating can optionally be masked to prevent the application of coating materials to the masked areas, and/or portions of applied coating materials can be removed to selectively leave a layer including the releasable component or other coating in a desired region or regions of the device.

The layer including the nitrite ion can be constituted entirely of the nitrite compound, or may, for example, include a biostable polymer, where the polymer remains attached to the device structure as nitrite ion is released. Alternatively, or in addition to the biostable polymer, this layer may include a bioabsorbable polymer. Such a polymer layer can include a polymeric matrix, e.g. made using a suitable polymer as identified herein, and in certain forms will be a porous layer that releasably contains an admixture including the nitrite compound in the pores thereof.

In certain embodiments, the nitrite ion is contained within the structure of the implantable device. For example, in those devices including a polymer component to the base structure, the nitrite ion may be included in the mixture inserted in a mold to form at least part of the structure of the device. In certain embodiments, a mixture including the nitrite ion and a polymer is extruded to form at least part of the structure of the device. In other embodiments, the releasable nitrite ion is imbibed into pores of a polymeric component of the device after this component is formed.

In certain aspects, a coated medical device as described herein, preferably comprising a stent and/or balloon catheter carrying the nitrite ion, can be configured to, and used to, treat any suitable body passage in a manner including release of the nitrite ion to the wall tissue of the body passage. The body passage may for example be a vein, artery, biliary duct, ureteral vessel, body passage or portion of the alimentary canal. A coated medical device as described herein may be used to treat, for example, a coronary artery, carotid artery, or a peripheral artery or vein, including as examples a renal artery or vein, iliac artery or vein, femoral artery or vein, popliteal artery or vein, subclavian artery or vein, intercranial artery or vein, aorta, vena cava, or others. In preferred embodiments, the coated medical device will treat or prevent stenosis or restenosis in a body passage such as any of those identified herein, although treatment of other conditions is contemplated for other embodiments of the invention. In certain embodiments, the coated medical device is configured to, and used to treat a narrowing of a peripheral artery or vein. Examples of such arteries include, but are not limited to, the femoral artery, the superficial femoral artery (artery below the branch for the profunda femoris artery), the popliteal artery and the infra-popliteal artery. Examples of such veins include, but are not limited to, the common iliac vein, external iliac vein, femoral vein, the popliteal vein and the lesser/greater saphenous vein.

Figure 1:
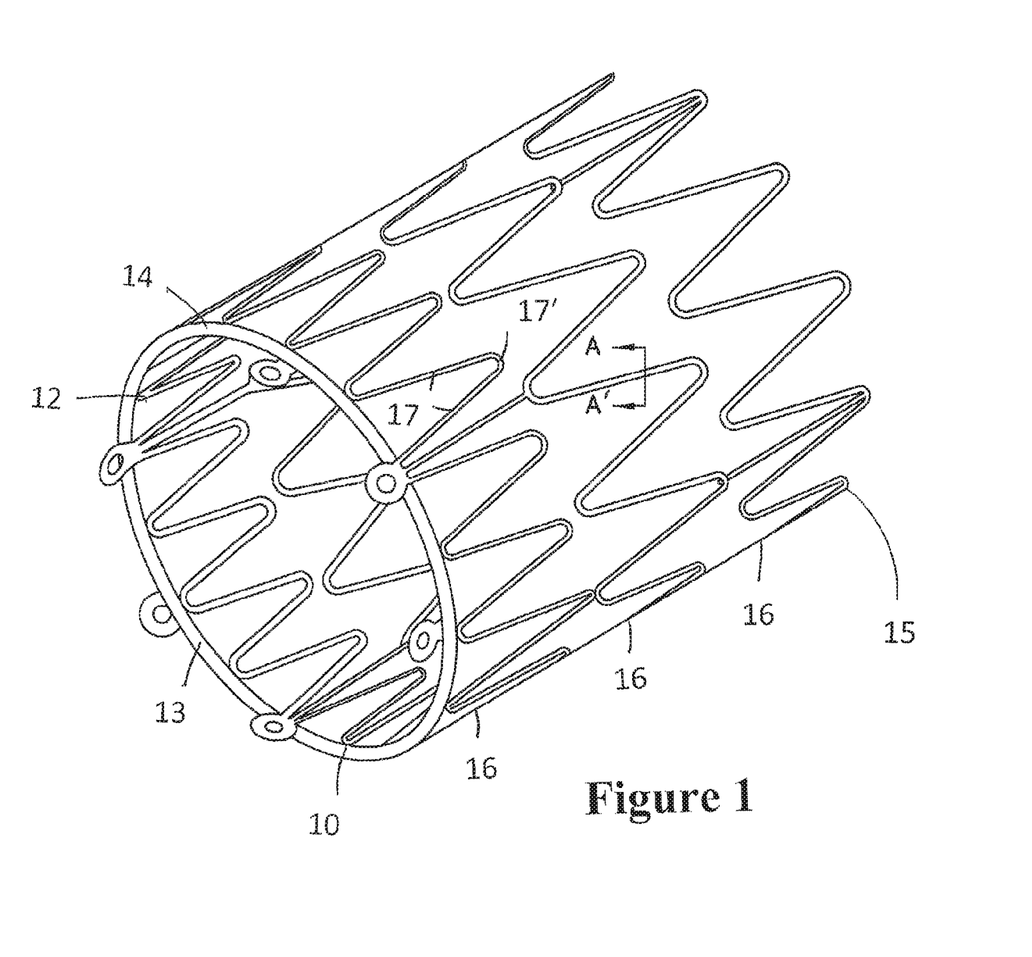
FIG. 1 is a schematic illustration of a coated stent.
Figure 2:
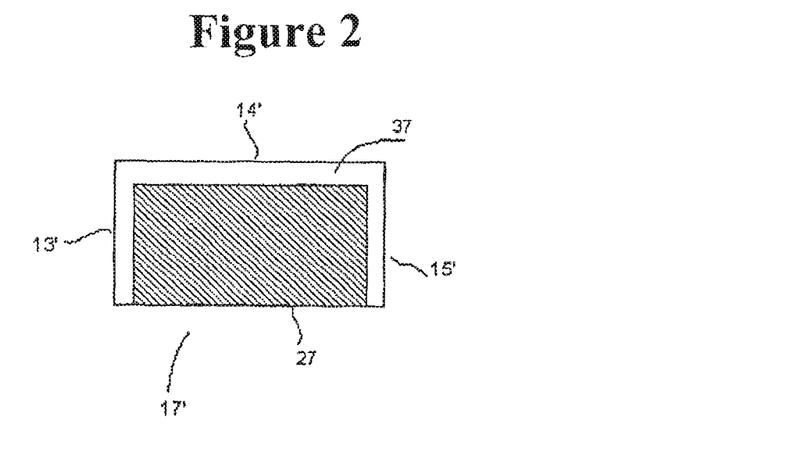
FIG. 2 shows a cross sectional view of a portion of the stent of FIG. 1.

In one embodiment of the present invention, the medical device is, or includes, a vascular stent. FIGS. 1 and 2 are schematic illustrations of one embodiment of a self-expanding vascular stent 10 having a luminal surface 12 and a coating 37 applied to the abluminal surface 14. The vascular stent 10 extends from a proximal end 13 to a distal end 15. The vascular stent 10 has a tubular shape formed from a series of joined hoops 16 formed from interconnected struts 17 and bends 18, and defines the interior lumen. The stent may be self-expanding or balloon-expandable and may be a bifurcated stent, a coronary vascular stent, a urethral stent, a ureteral stent, a biliary stent, a tracheal stent, a gastrointestinal stent, or an esophageal stent, for example.

FIG. 2 shows a cross section along line A-A' of coated strut 17' from the vascular stent 10 shown in FIG. 1. Referring to FIG. 2, the strut 17' can have any suitable cross sectional configuration, such as a rectangular cross section, and can be formed from any suitable material 27 such as those disclosre herein, including a nickel titanium alloy, stainless steel or a cobalt chromium alloy. The abluminal surface 14', including the proximal edge 13' and distal edge 15', are coated with the coating 37 including a nitrite ion as disclosed herein adhered to the abluminal surface of the vascular stent 10. In some embodiments, the luminal surface is not coated with coating 37. However, the present invention also includes those embodiments where coating 37 is also present on the luminal surface.

In some embodiments, the implantable device, such as vascular stent 10, may include a coating also containing a carrier, such as a biostable or biodegradable polymeric or non-polymeric carrier, which controls the release of the nitrite ion from the device. For example, the carrier may decrease the rate of release of the nitrite ion, allowing for elution of the nitrite ion over an extended period of time. In other embodiments, the coating is free of such a carrier. For example, the coating may be free of any component that decreases the rate of release of the nitrite ion over that observed when only the nitrite compound is present on the surface of the device. In some embodiments, a layer of the nitrite compound without a carrier is present and forms the outermost layer of the device. In other embodiments, the device coating layer containing the nitrite compound consists essentially of the nitrite compound. For the purposes of the present disclosure the coating layer is considered to consist essentially of the nitrite compound when it is free of any carrier material that reduces the rate of release of the nitrite ion into the physiological environment of the vascular system by more than 5 percentage compared to the rate of release obtained when the coating layer includes only the nitrite compound.

Figure 3:
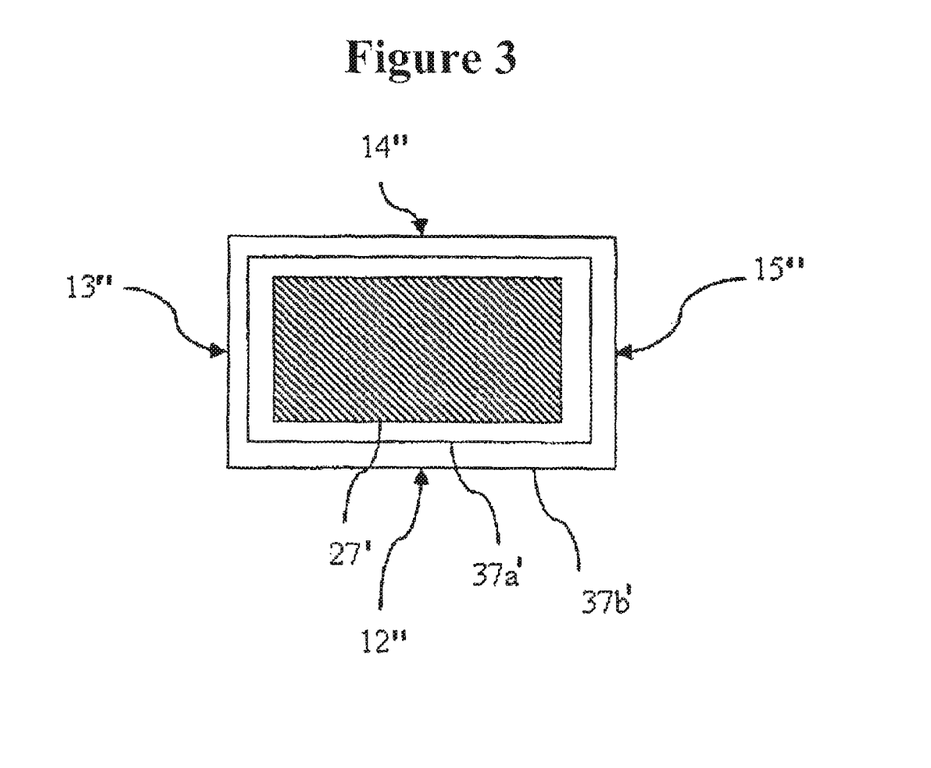
FIG. 3 shows an alternative cross sectional view of a portion of the stent of FIG. 1.

FIG. 3 shows an alternative cross-sectional view of the portion A-A' of the medical device strut 17' shown in FIG. 2. Referring to FIG. 3, the abluminal surface 14", including the proximal edge 13" and distal edge 15", and the luminal surface 12" are coated with a two layer coating including a first layer 37a' and a second layer 37b'. However, embodiments including such a two-layer coating having an uncoated luminal surface are also within the scope of the present invention. Preferably, the first layer 37a' includes the nitrite compound as disclosed herein and may, or may not, include a carrier material. The second layer 37b' may include a release modifying agent, such as a porous material, a biodegradable material, or other component adapted to alter the rate of release of the nitrite ion. For example, second layer 37b' may include a non-degradable or biodegradable polymeric material. In preferred embodiments, second layer 37b' does not include the nitrite compound.

The present invention also includes devices having multiple layers include the nitrite compound. These layers may or may not include a carrier as described herein and may are may not be separated by layers that do not include the nitrite compound.

Other coating configurations are also encompassed in the present invention. For example, additional coating layers may be present, including multiple layers including the same or different nitrite compounds. Such coating layers may or may not be separated by layers not including the nitrite compound(s).

In other embodiments, instead of, or as well as, being present on a surface of the device, the nitrite compound may be present in holes, wells or slots formed in a surface of the device. Examples of such coating configurations are disclosed in U.S. Pat. No. 7,896,914, the contents of which are incorporated by reference.

Figure 4:
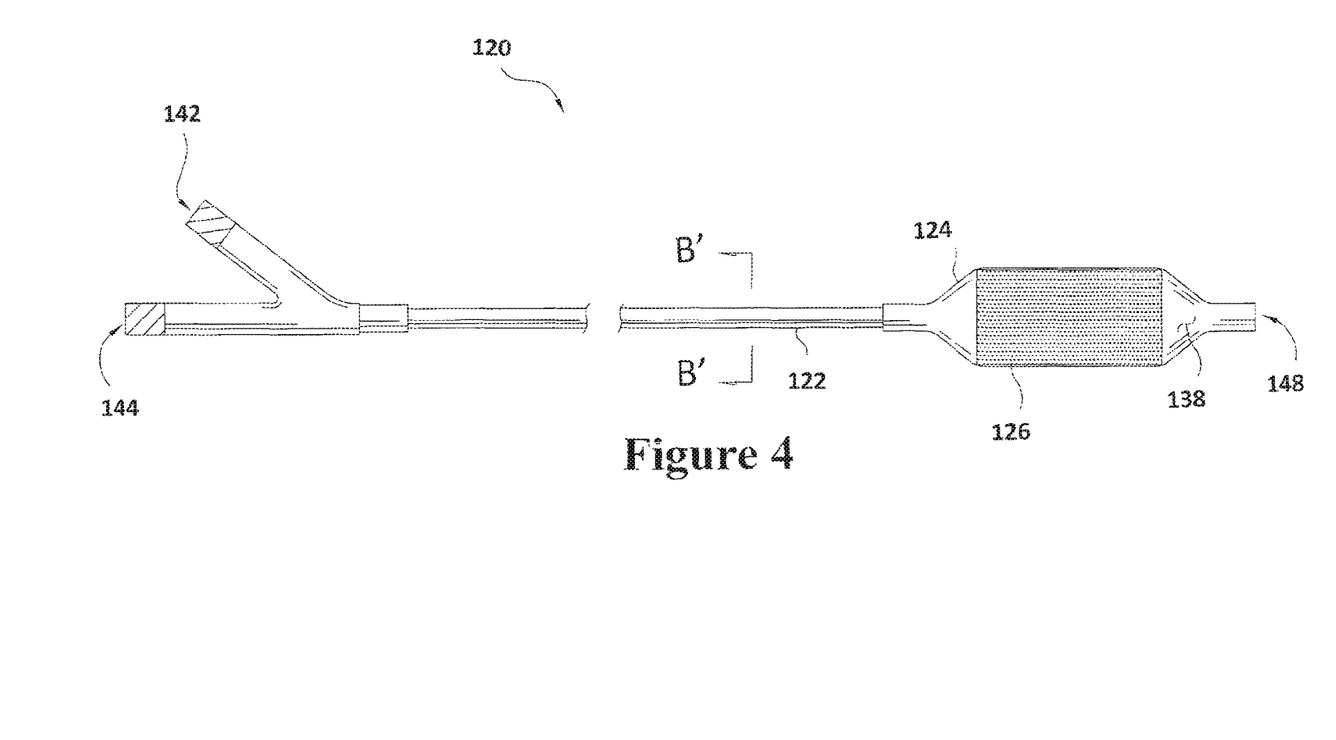
FIG. 4 provides a perspective view of a drug-delivering balloon catheter in accordance with one embodiment of the invention in an inflated condition.
Figure 5:
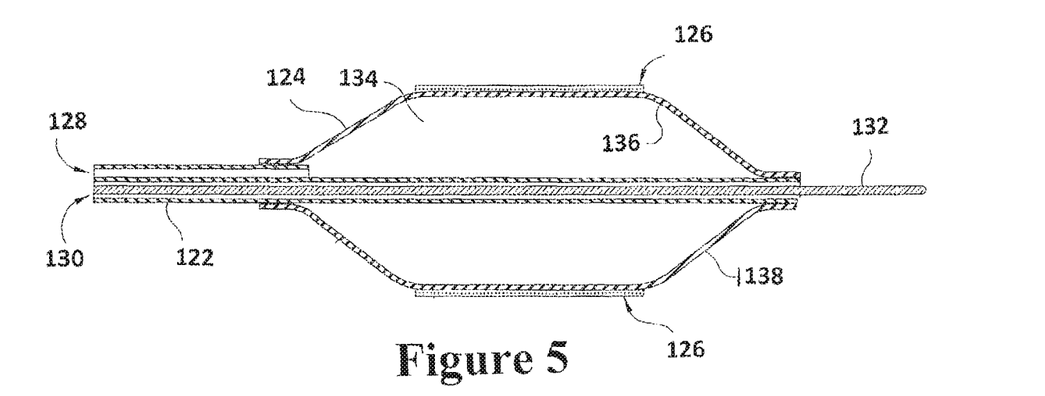
FIG. 5 provides a cross-sectional view of the balloon-mounted region of the balloon catheter of FIG. 4 taken along a central longitudinal axis.
Figure 6:
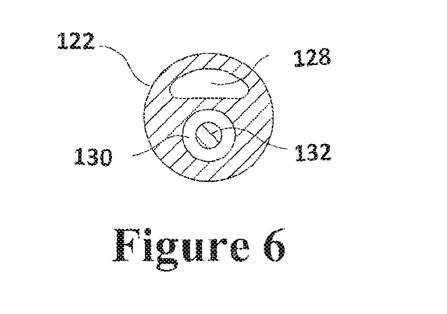
FIG. 6 provides a cross-sectional view of the catheter shaft of the balloon catheter of FIG. 1 taken along line B'-B' and viewed in the direction of the arrows.

With reference now to FIGS. 4-6, shown is one embodiment of a drug-delivering balloon catheter 120 in accordance with one embodiment of the invention. FIG. 6 shows a cross-sectional view of the portion B-B'. Balloon catheter 120 includes a catheter shaft 122 and a balloon 124 mounted thereon. A coating 126 including a layer containing a nitrite compound as described herein is carried by balloon 124. Catheter shaft 122 includes a first lumen 128 and second lumen 130. Lumen 128 is configured for inflation of balloon 124, and lumen 130 is configured to receive a guide wire 132 or other guide member to be used in conjunction with balloon catheter 120. Balloon 124 includes an interior region 134 designed to receive a liquid or other fluid for inflation of balloon 124. Balloon 124 has an inner wall 136 bounding balloon interior 134, and an outer wall surface 138. Coating 126 is adhered to outer wall surface 138 of balloon 124.

Coating 126 may be a single layer coating or multiple layer coating as disclosed herein. In some embodiments, the layer(s) including the nitrite compound also includes an excipient that increases the rate of release of the nitrite ion from the device. Such excipients include, but are not limited to, gallate-containing compounds, such as those disclosed in U.S. Pat. No. 9,180,226, the contents of which are incorporated by reference.

Methods of Delivery and Treatment

Another aspect of the invention provides a method of delivering an nitrite ion to the body of a human or veterinary patient including implanting an medical device having any of the configurations described herein into the body of the patient and maintaining the device within the patient for a time sufficient to deliver the nitrite ion to the body of the patient.

Yet another aspect of the invention provides a method of treating a disease or condition involving inserting into a human or veterinary patient an implantable medical device having any of the configurations described herein and maintaining the device within the patient for a time sufficient to deliver a therapeutically effective amount of the nitrite ion to the patient.

For example, when the implantable medical device is a vascular stent of balloon catheter coated as described herein, the method of treatment can involve implanting the stent, or delivering the balloon, into the coronary or peripheral vascular system of the patient and allowing a therapeutically effective amount of the nitrite ion to be released from the stent in a controlled manner to treat the disease or condition. In one preferred embodiment, the disease or condition is restenosis.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A medical device comprising:
   a base structure having an external surface and an interior surface, and
   a coating on the external surface comprising a compound comprising an ionically bonded nitrite ion, the nitrite ion being bound in such a way that it is released from the device as a free ion after introduction into a body of a patient, wherein the implantable medical device is free of a nitric oxide generator.

2. The medical device of claim 1, wherein the compound is an organic compound.

3. The medical device of claim 2, wherein the organic compound is selected from the group consisting of a secondary amine nitrite, dicyclohexylamine nitrite, a quarternary ammonium nitrite and tetrabutylammonium nitrite.

4. The medical device of claim 1, wherein the compound is an inorganic compound.

5. The medical device of claim 4, wherein the inorganic compound is selected from the group consisting of nitrous acid, ammonium nitrite, and a metal nitrite selected from the group consisting of sodium nitrite, lithium nitrite, potassium nitrite, calcium nitrite, magnesium nitrite, and nickel nitrite.

6. The medical device of claim 1, wherein the coating consists essentially of the compound.

7. The medical device of claim 1, wherein the coating further comprises a polymeric or non-polymeric carrier matrix.

8. The medical device of claim 1, wherein the coating is free of a polymer or non-polymer carrier matrix.

9. The medical device of claim 1, wherein the medical device is selected from the group consisting of a stent, a vascular stent, a ureteral stent, a catheter, a balloon, a balloon catheter, a stent graft, a wire guide, and a cannula.

10. The medical device of claim 9, wherein the medical device is a stent.

11. The medical device of claim 9, wherein the stent is a vascular stent.

12. The medical device of claim 9, wherein the medical device is a balloon catheter.

13. The medical device of claim 1, wherein the coating further comprises a drug is selected from the group consisting of an immunosuppressive agent, an antiproliferative agent, a microtubule stabilizing agent, a restenosis-inhibiting agent, and an inhibitor of the mammalian target of rapamycin.

14. The medical device of claim 1, wherein the wherein the coating further comprises a taxane compound.

15. The medical device of claim 13, wherein the taxane compound is paclitaxel.

16. A medical device comprising:
a vascular stent comprising a base structure having an external surface and an interior surface, and
a coating on the external surface comprising a compound comprising an ionically bound nitrite ion, the nitrite ion being bound in such a way that it is released from the device as a free ion after introduction into a body of a patient, wherein the implantable medical device is free of a nitric oxide generator and wherein the compound is an inorganic nitrite.

\* \* \* \* \*